(12) United States Patent
Friedman et al.

(10) Patent No.: US 8,323,352 B2
(45) Date of Patent: Dec. 4, 2012

(54) METHOD FOR TREATMENT AND PREVENTION OF PARASTOMAL HERNIAS

(75) Inventors: Evan Friedman, Montvale, NJ (US); Elizabeth Cerullo, Hoboken, NJ (US)

(73) Assignee: Lifecell Corporation, Branchburg, NJ (US)

( * ) Notice: Subject to any disclaimer, the term of this patent is extended or adjusted under 35 U.S.C. 154(b) by 444 days.

(21) Appl. No.: 12/621,786

(22) Filed: Nov. 19, 2009

(65) Prior Publication Data

US 2010/0137677 A1    Jun. 3, 2010

Related U.S. Application Data

(60) Provisional application No. 61/116,538, filed on Nov. 20, 2008.

(51) Int. Cl.
*A61F 2/02* (2006.01)
(52) U.S. Cl. .................................................. 623/23.72
(58) Field of Classification Search .... 623/23.72–23.73, 623/23.75–23.76; 606/151, 153; 600/29–30, 600/37; 128/334 R, 898
See application file for complete search history.

(56) References Cited

U.S. PATENT DOCUMENTS

| | | | |
|---|---|---|---|
| 4,796,603 A | 1/1989 | Dahlke et al. | |
| 4,854,316 A * | 8/1989 | Davis | 606/153 |
| 5,254,133 A * | 10/1993 | Seid | 606/215 |
| 5,336,616 A | 8/1994 | Livesey et al. | |
| 5,364,756 A | 11/1994 | Livesey et al. | |
| 5,634,931 A | 6/1997 | Kugel | |
| 5,780,295 A | 7/1998 | Livesey et al. | |
| 5,972,007 A | 10/1999 | Sheffield et al. | |
| 6,113,623 A | 9/2000 | Sgro | |
| 6,174,320 B1 | 1/2001 | Robert et al. | |
| 6,179,872 B1 | 1/2001 | Bell et al. | |
| 6,194,136 B1 | 2/2001 | Livesey et al. | |
| 6,197,036 B1 | 3/2001 | Tripp et al. | |
| 6,381,026 B1 | 4/2002 | Schiff et al. | |
| 6,599,318 B1 | 7/2003 | Gabbay | |
| 6,610,006 B1 | 8/2003 | Amid et al. | |
| 6,638,284 B1 | 10/2003 | Rousseau et al. | |
| 6,726,660 B2 | 4/2004 | Hessel et al. | |
| 6,790,213 B2 | 9/2004 | Dennis et al. | |
| 6,833,408 B2 | 12/2004 | Sehl et al. | |
| 6,933,326 B1 | 8/2005 | Griffey et al. | |
| 7,105,001 B2 | 9/2006 | Mandelbaum | |
| 7,235,295 B2 | 6/2007 | Laurencin et al. | |

(Continued)

FOREIGN PATENT DOCUMENTS

JP    2002-186581 A    7/2002

(Continued)

OTHER PUBLICATIONS

International Search Report and Written Opinion issued by Korean Intellectual Property Office for International Application No. PCT/US2009/065087, mailing date Aug. 3, 2010.

(Continued)

*Primary Examiner* — Melanie Tyson
*Assistant Examiner* — Son Dang
(74) *Attorney, Agent, or Firm* — Finnegan, Henderson, Farabow, Garrett & Dunner, L.L.P.

(57) ABSTRACT

A method and device for preventing or treating parastomal hernia is provided. The method can include positioning a graft material between a rectus sheath and a rectus abdominus muscle surrounding a stoma.

16 Claims, 3 Drawing Sheets

U.S. PATENT DOCUMENTS

| | | | |
|---|---|---|---|
| 7,358,284 | B2 | 4/2008 | Griffey et al. |
| 2002/0099344 | A1 | 7/2002 | Hessel et al. |
| 2002/0103542 | A1 | 8/2002 | Bilbo |
| 2003/0035843 | A1 | 2/2003 | Livesey et al. |
| 2003/0119985 | A1 | 6/2003 | Sehl et al. |
| 2003/0143207 | A1 | 7/2003 | Livesey et al. |
| 2003/0225355 | A1 | 12/2003 | Butler |
| 2004/0078077 | A1 | 4/2004 | Binette et al. |
| 2004/0078089 | A1 | 4/2004 | Ellis et al. |
| 2005/0009178 | A1 | 1/2005 | Yost et al. |
| 2005/0028228 | A1 | 2/2005 | McQuillan et al. |
| 2005/0043716 | A1 | 2/2005 | Frimer |
| 2005/0054771 | A1 | 3/2005 | Sehl et al. |
| 2005/0058629 | A1 | 3/2005 | Harmon et al. |
| 2005/0288691 | A1 | 12/2005 | Leiboff |
| 2006/0073592 | A1 | 4/2006 | Wendell et al. |
| 2006/0105026 | A1 | 5/2006 | Fortune et al. |
| 2006/0106419 | A1 | 5/2006 | Gingras |
| 2006/0247206 | A1 | 11/2006 | Feins |
| 2006/0276908 | A1 | 12/2006 | Sogaard-Andersen et al. |
| 2007/0111937 | A1 | 5/2007 | Pickar et al. |
| 2007/0202173 | A1 | 8/2007 | Cueto-Garcia |
| 2007/0248575 | A1 | 10/2007 | Connor et al. |
| 2007/0293878 | A1 | 12/2007 | Butsch |
| 2008/0027542 | A1 | 1/2008 | McQuillan et al. |
| 2008/0033461 | A1 | 2/2008 | Ferdinand et al. |
| 2008/0071300 | A1 | 3/2008 | Popadiuk et al. |
| 2008/0091277 | A1 | 4/2008 | Deusch et al. |
| 2008/0095819 | A1 | 4/2008 | Gourdie et al. |
| 2008/0113035 | A1 | 5/2008 | Hunter |
| 2008/0131509 | A1 | 6/2008 | Hossainy et al. |
| 2008/0147199 | A1 | 6/2008 | Yost et al. |
| 2008/0167729 | A1 | 7/2008 | Nelson et al. |
| 2009/0035289 | A1 | 2/2009 | Wagner et al. |
| 2009/0306790 | A1 | 12/2009 | Wendell |

FOREIGN PATENT DOCUMENTS

| | | |
|---|---|---|
| WO | WO 00/16822 | 3/2000 |

OTHER PUBLICATIONS

Aycock et al., "Parastomal Hernia Repair With Acellular Dermal Matrix," *J. Wound Ostomy Continence Nurs.* (2007), p. 521-523, 34(5).

Greenstein et al., "Parastomal Hernia Repair Using Cross-Linked Porcine Dermis: Report of a Case," *Surg. Today* (2008), p. 1048-1051, 38.

Hammond et al., "Human in vivo Cellular Response to a Cross-Linked Acellular Collagen Implant," *British Journal of Surgery* (2008), p. 438-446, 95.

Hammond et al., "Parastomal Hernia Prevention Using a Novel Collagen Implant: A Randomised Controlled Phase 1 Study," *Hernia* (2008), p. 475-481, 12.

Inan et al., "Laparoscopic Repair of Parastomal Hernia Using a Porcine Dermal Collagen (Permacol™) Implant," *Dis. Colon Rectum* (2007), p. 1465, 50.

Israelsson, "Preventing and Treating Parastomal Hernia," *World J. Surg.* (2005), p. 1086-1089, 29.

Jänes et al., "Randomized Clinical Trial of the Use of a Prosthetic Mesh to Prevent Parastomal Hernia," *British Journal of Surgery* (2004), p. 280-282, 91.

Kasperk et al., "The Repair of Large Parastomal Hernias Using a Midline Approach and a Prosthetic Mesh in the Sublay Position," *The American Journal of Surgery* (2000), p. 186-188, 179.

Kish et al., "Acellular Dermal Matrix (AlloDerm): New Material in the Repair of Stoma Site Hernias," *The American Surgeon* (2005), p. 1047-1050, 71.

Lochan et al., "Letter 1: Parastomal Hernia," *Br. J. Surg.* (2003), p. 784-793, 90, abstract.

Petersen et al., "Ventral Rectus Fascia Closure on Top of Mesh Hernia Repair in the Sublay Technique," *Plastic and Reconstructive Surgery* (2004), p. 1754-1760, 114(7).

\* cited by examiner

METHOD FOR TREATMENT AND PREVENTION OF PARASTOMAL HERNIAS

This application claims priority to U.S. Provisional Application No. 61/116,538, filed Nov. 20, 2008, which is incorporated herein by reference in its entirety.

BACKGROUND

Ostomies are commonly used to reroute intestine or urinary structures that are permanently or temporarily unable to function properly. In such a procedure, a connection between a body passage or cavity and the body wall is surgically created. This connection, generally referred to as a stoma, allows waste products to be expelled through an opening in the body wall. Ostomies can typically include, for example, colostomies, ileostomies, and urostomies.

An ostomy can create a weakened area in the abdominal wall surrounding the opening. Over time intra-abdominal contents may protrude into or next to the stoma, creating parastomal hernia. Stoma hernias are uncomfortable and can become extremely inconvenient because of poor appliance sealing or leaking. In some instances, a loop of herniated bowel can become trapped, potentially leading to a serious condition, known as strangulation, where the blood supply to the bowel is compromised. In some cases, surgical intervention is required to repair parastomal hernias. However, repair of hernias is a major surgical operation, and currently available procedures have had limited success in preventing additional recurrence.

Accordingly, there remains a need for improved methods and devices for preventing or repairing parastomal hernias. The present disclosure provides methods and devices for prophylactic treatment or repair of parastomal hernia.

SUMMARY

According to certain embodiments, a method of preventing parastomal hernia is provided. The method comprises selecting a graft material for prophylactic reinforcement of a stoma site and forming an opening in an abdominal wall traversing the rectus abdominus. A space between the rectus abdominus muscle and the rectus sheath of the abdominal wall surrounding the opening is formed. The graft material is inserted into the space between the rectus abdominus muscle and the rectus sheath, and a portion of a hollow organ is passed through the graft material and the opening in the abdominal wall to form a stoma between the hollow organ and the abdominal wall with the graft material surrounding the hollow organ. A portion of the hollow organ is attached to the abdominal wall to produce an ostomy. In one aspect, the graft material is not actively fixed to the rectus abdominus muscle or the rectus sheath.

According to certain embodiments, a method of repairing parastomal hernia is provided. The method comprises selecting a graft material for repairing of a stoma site and forming a space between the rectus abdominus muscle and the rectus sheath of the abdominal wall surrounding the stoma site. The graft material is inserted into the space between the rectus abdominus muscle and the rectus sheath to surround the stoma site, wherein the graft material is not actively fixed to the rectus abdominus muscle or the rectus sheath.

According to certain embodiments, a device for repairing or reducing the incidence of parastomal hernia is provided. The device comprises a graft material, wherein the material includes an elongated sheet having a substantially central opening, the central opening being formed by two or more elongated slits positioned diagonally across the elongated sheet to form a substantially "x"-shaped configuration.

It is to be understood that both the foregoing general description and the following detailed description are exemplary and explanatory only and are not restrictive of the invention, as claimed.

The accompanying drawings, which are incorporated in and constitute a part of this specification, illustrate methods and embodiments of the invention and together with the description, serve to explain the principles of the various aspects of the invention.

DETAILED DESCRIPTION

The present disclosure provides methods for preventing or repairing parastomal hernias. In some embodiments, the method includes positioning a graft material between the rectus abdominus muscle and the surrounding rectus sheath. In some embodiments, the graft is positioned between the muscle and sheath without the use of active fixation, such as sutures, staples, or clips. In certain embodiments, the graft is positioned between the posterior sheath of the rectus abdominus and the rectus muscle. In other embodiments, the sheath is positioned between the anterior sheath and the rectus muscle. In some embodiments, grafts can be positioned between both the anterior sheath and the rectus muscle and the posterior sheath and rectus muscle.

In some embodiments, a graft can be positioned between the rectus sheath and corresponding rectus muscle to prophylactically treat or prevent parastomal hernia. In some embodiments, the selected graft material is immunologically inert or has reduced immunogenicity so as to prevent an immune response in the body. In some embodiments, the graft material is non-synthetic. In one embodiment, the graft material is a collagenous material. In certain embodiments, the graft can include an acellular tissue matrix. In one embodiment, the acellular tissue matrix is a non cross-linked matrix. In another embodiment, the acellular tissue matrix can include a dermal matrix. Further, in certain embodiments, the material can be selected to provide a structural reinforcement to the abdominal wall surrounding a surgically created stoma. Additionally, in some embodiments, the material can be selected to facilitate tissue ingrowth after implantation. The material provides rapid tissue ingrowth, thereby securing the material in place without the need for active fixation such as sutures, clips, or staples.

In one embodiment of the present disclosure, the material may be derived from porcine dermis that has been processed to remove cells and reduce immnogenicitiy. For example, one suitable porcine-derived tissue is Strattice™, which is a porcine dermal tissue produced by Lifecell Corp, Branchburg, N.J. The tissue matrix may be derived from porcine skin by removing the epidermis while leaving the dermal matrix substantially intact. Further, the porcine-derived tissue matrix may facilitate tissue ingrowth and remodeling with the patient's own cells. In other embodiments, the material can include a collagenous matrix derived from human cadaver skin (e.g. AlloDerm™, Lifecell Corp, Branchburg, N.J.) that has been processed to remove both the epidermis and cells.

Figure 1:
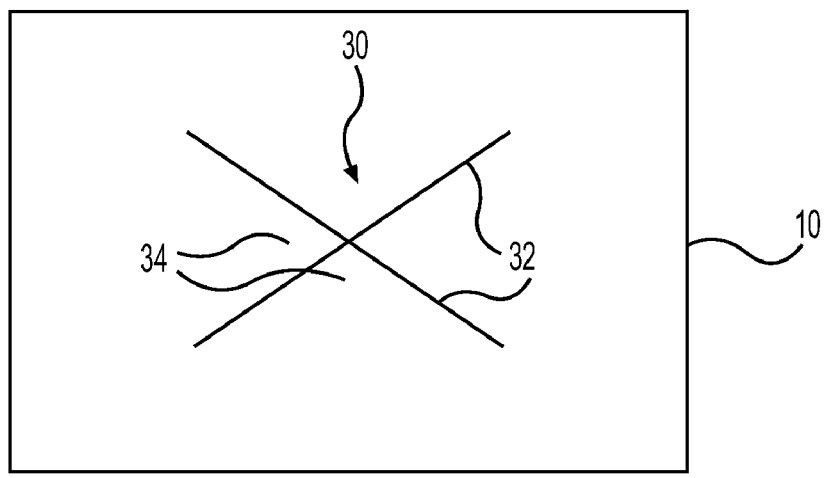
FIG. 1 is a top view of an exemplary embodiment of a graft material for preventing or repairing parastomal hernia, according to certain embodiments.

In some embodiments, the material can be selected to facilitate implantation during a primary ostomy procedure or for repair of an existing parastomal hernia. For example, FIG. 1 illustrates a graft material 10 for treatment or prevention of parastomal hernia, according to certain embodiments. As shown, the material can include a single sheet of material with an opening 30 therethrough to allow passage of a portion of a hollow abdominal or pelvic organ (e.g., small or large intestine or urinary structures).

As shown, in some embodiments, the graft material 10 can include an approximately square material with two diagonally intersecting lines 32. As shown, the lines 32 can form an opening 30 having a substantially "x"-shaped configuration. In some embodiments, the lines 32 can include preformed slits that form the opening 30. In some embodiments, the lines 32 can be surface markings or perforations that are not yet cut, but may serve as a guide so that a physician can cut the material 10 to produce the opening 30.

As shown, the lines 32 extend diagonally across the material 10 from a first corner towards a corresponding opposite corner. This configuration may be desirable for some embodiments as the distance across the material 10 is longest in this direction. Consequently, if a surgeon should need to enlarge one or more of the lines or slits 32 there will be more surrounding material available between the end of the enlarged line or slit 32 and the corner or edge of the material 10. In this way, the surgeon has more flexibility in controlling the slit size, and more supporting material remains between the slit 32 and edge of the material 10.

As described in more detail below, the opening configuration, including lines or slits 32 can facilitate material preparation during surgery. In some embodiments, the "x"-shaped configuration provides added support to the stoma and/or surrounding tissue. For example, the lines or slits 32 produce tabs or flaps 34 that substantially surround the organ passing through the opening 30, thereby providing support to the tissue of the hollow organ forming the stoma.

As stated above, in some embodiments, the graft material 10 can be positioned between the rectus sheath and rectus muscle. In some embodiments, the graft material is positioned without the use of active fixation, such as sutures, clips, or staples that contact the material to secure the material in place.

Figure 2:
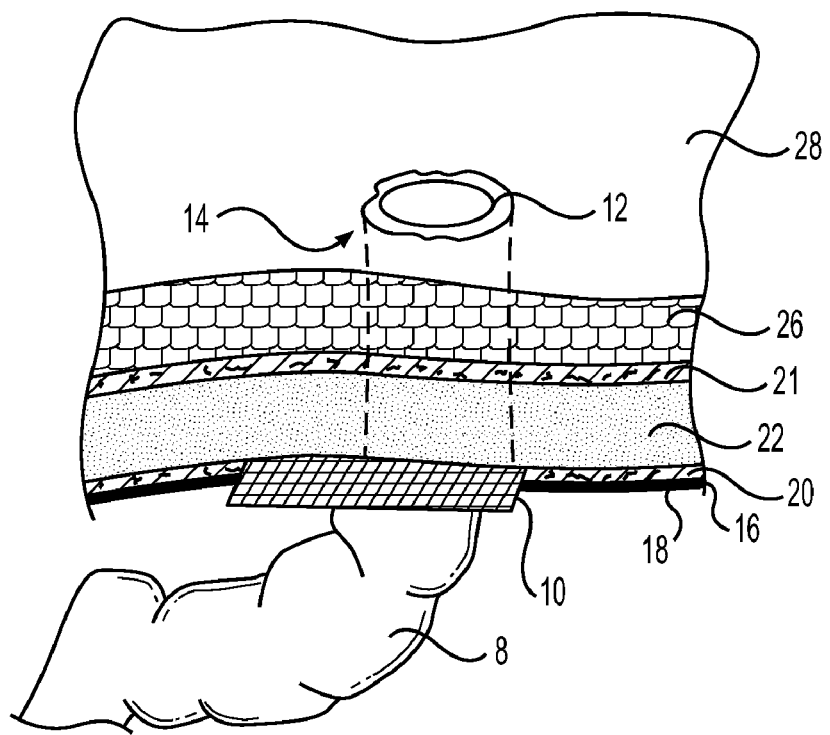
FIG. 2 is a perspective, cut-away view of a graft material positioned between a posterior rectus sheath and a rectus abdominus muscle near a stoma, according to certain embodiments.

FIG. 2 illustrates a perspective, cut-away view of an abdominal wall with a graft material 10 implanted between the posterior rectus sheath and rectus abdominus muscle around a stoma, according to certain embodiments. As shown in FIG. 2, the stoma 14 forms a connection between a hollow intra-abdominal or pelvic organ 8 (such as, a bowel or urinary structure) and the surface of the body. As illustrated in FIG. 2, the stoma 14 allows rerouting of a portion of the hollow organ through an opening 12 in the abdominal wall. The portion of the large intestine that forms the stoma 14 traverses each of the abdominal tissue layers where the stoma 14 is formed. As shown, the stoma 14 is positioned at the level of the rectus muscle above the arcuate line, and the hollow organ 8 traverses the peritoneum 16, the transversalis fascia 18, the posterior rectus sheath 20, the rectus muscle 22, the anterior rectus sheath 21, subcutaneous fat 26, and skin 28. The hollow organ 8 also passes through the opening 30 in the graft material 10 implanted between the posterior rectus sheath 20 and rectus abdominus muscle 22. In one embodiment, the material graft 10 is not actively fixed within this anatomical position.

The methods of the present disclosure can be used to prevent or treat parastomal hernia associated with any type of ostomy, including, for example, ileostomies, colostomies, and/or urostomies. Further, the terms hollow organ, hollow abdominal organ, and hollow cavity will be understood to refer to any hollow abdominal or pelvic organ or tissue, including any gastrointestinal (e.g., intestine of any kind) or urinary structure (e.g. ureter or bladder) that may be used in the creation of a stoma or ostomy procedure.

Figure 3:
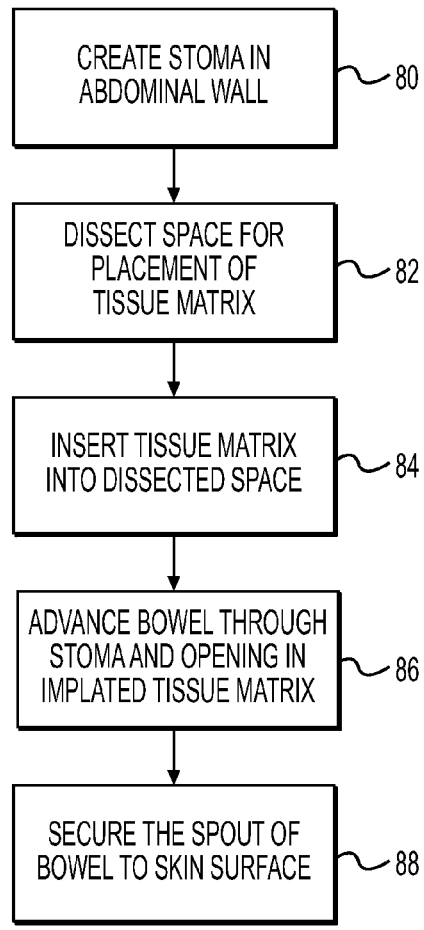
FIG. 3 is a flowchart of a method for preventing or treating parastomal hernia, according to certain embodiments.

As described above, the methods of the present disclosure allow prophylactic treatment of parastomal hernia during primary ostomy procedures or during a stoma relocation procedure. In some embodiments, the methods of the present disclosure allow prophylactic parastomal hernia treatment with little to moderate additional surgical steps, operative time, and/or trauma to the patient. FIG. 3 illustrates methods for preventing or reducing the rate of parastomal hernia formation. As shown in step 80, the method begins with the formation of an opening or incision in the abdominal wall through which a section of the hollow organ 8 is to be externalized. The opening or incision can be formed using a number of different tools and at various stages in the surgical procedure. For example, in some embodiments, the opening is formed using a scalpel or with a pre-sized instrument (e.g., a trocar). In many cases, the ostomy is performed later in a surgical procedure, for example, after partial resection of a diseased organ or intestine. Therefore, generally, the opening or incision is produced after a primary incision has already been made for an open surgical procedure, or after laproscopic access has been obtained.

After the opening is formed in the abdominal wall, a potential space for the placement of the graft material 10 is created, as indicated in step 82. In some embodiments, the graft material 10 is positioned between the rectus sheath 20, 21 and the rectus abdominus muscle 22. Therefore, a surgeon may create a space for positioning the graft material 10 by separating or dissecting the posterior sheath 20, anterior sheath 21, or both the posterior 20 and anterior sheath 21 from the rectus muscle 22 in the area surrounding the stoma site 14.

Generally, the rectus sheath 20, 21 can be separated from the rectus abdominus muscle 22 using blunt dissection, which can be accomplished using a surgeon's finger or a blunt instrument. In some embodiments, the dissection is performed in all directions surrounding the stoma 14. In addition, the dissection can be performed by accessing the rectus sheath through the opening that is formed to produce the stoma. Alternatively, the dissection can be performed through the primary incision that has already been made for an open surgical procedure, or through laproscopic ports created for the earlier procedure.

Generally, the dissection will be performed to produce a space large enough to accommodate a selected graft size. For example, a suitable graft size will generally be about 6 cm×6 cm, square. However, in some embodiments, larger or smaller grafts may be selected based on patient size, previous surgeries, and/or other patient conditions. In addition, the graft material 10 can be rectangular or have another configuration. In some embodiments, the surgeon will trim the graft material 10 to a desired shape and/or size prior to implantation or in situ.

After formation of the space between the rectus sheath 20, 21 and rectus abdominus 22, a sterile sheet of the graft material 10 is then inserted into the dissected space, as shown in step 84. As described above, the sheet can include a preformed opening 30 that is generally positioned so that the opening is aligned with the incision or opening traversing the abdominal wall.

Next, the portion of the hollow organ 8 that will form the stoma 14 is passed through the opening 30 in the graft material 10 and through the opening 12 in the abdominal wall, as shown in step 86. In this way, the hollow organ 8 passes through the opening 30 so that the stoma site is surrounded by the graft material 10. In addition, the flaps 34 of the "x"-shaped central portion of the material 10 will be positioned along the side walls of the portion of the hollow organ traversing the opening 12. In some embodiments, the flaps 34, being positioned alongside the side walls of the organ, can serve to stabilize the organ and provide additional reinforcement to prevent parastomal hernia.

Finally, the stoma formation is completed by securing the portion of the hollow organ to skin or tissue surrounding the opening in the abdominal wall, thereby completing the ostomy. It should be noted that, in this way, the graft material 10 is secured in the abdominal wall surrounding the stoma without the use of sutures or other active fixation devices. The graft material 10 is sandwiched in between the rectus sheath 20, 21 and the rectus muscle 22, which inhibits dislodgement of the graft material after implantation.

Figure 4:
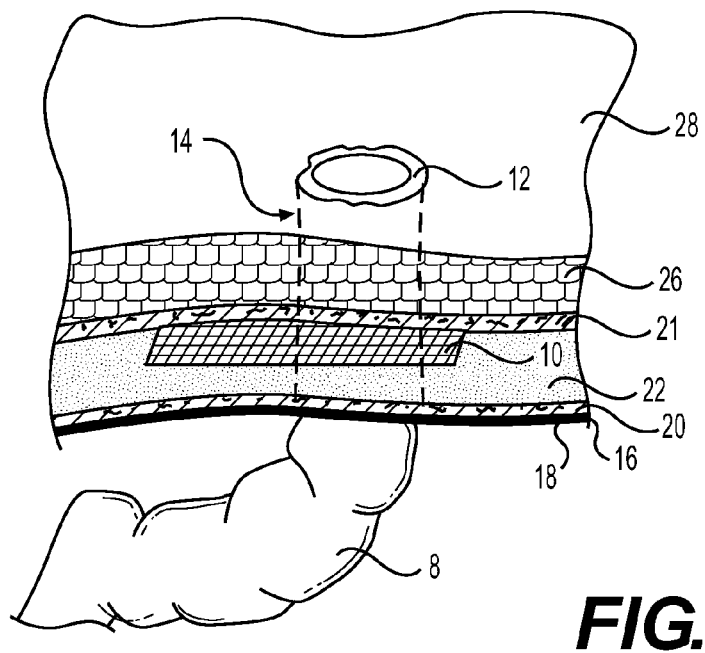
FIG. 4 is a perspective, cut-away view of a graft material positioned between an anterior rectus sheath and a rectus abdominus muscle near a stoma, according to certain embodiments.
Figure 5:
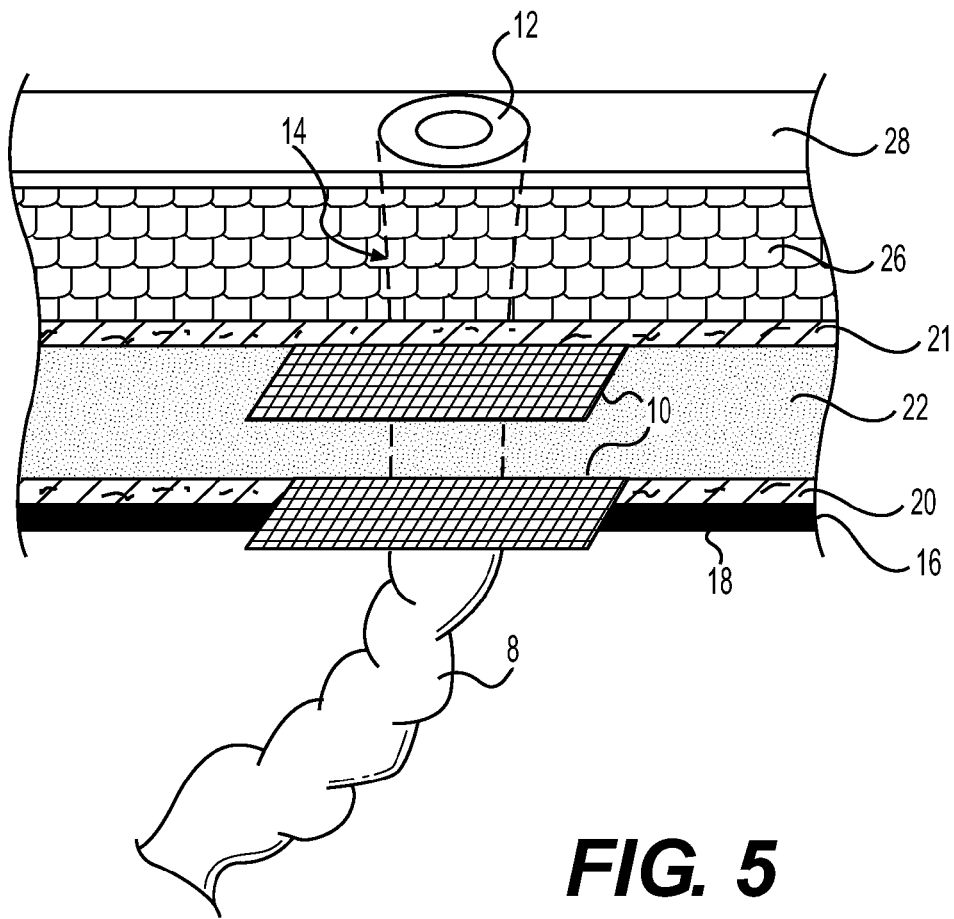
FIG. 5 is a perspective, cut-away view of a graft material positioned beneath both the anterior and posterior sheath of a rectus abdominus muscle near a stoma, according to certain embodiments.

In some embodiments, the graft material 10 can be implanted in a space dissected between the rectus abdominus muscle 22 and the anterior rectus sheath 21, as shown in FIG. 4. Generally, placement of the graft material 10 in this location can be performed using the same procedure outlined above for dissecting the space between the posterior sheath and rectus muscle for graft placement. Further, in some embodiments, as shown in FIG. 5, the graft material 10 can be positioned between the anterior sheath 21 and rectus muscle 22 and between the posterior sheath 20 and rectus muscle 22 to provide added support to prevent or treat parastomal hernia.

In some embodiments, the methods of the present disclosure include repair of existing parastomal hernia. Treatment of existing parastomal hernia can be performed in a method similar to that used to prevent parastomal hernia formation after primary stoma formation. As with preventative treatments, in some embodiments, parastomal hernia repair can be accomplished by placing a graft material 10 between a portion of the rectus sheath 20, 21 and the rectus abdominus muscle 22 surrounding the stoma. In some embodiments, the graft material 10 can be positioned between the posterior sheath 20 and the rectus muscle 22. In some embodiments, the graft material 10 is positioned between the anterior sheath 21 and rectus muscle 20. In certain embodiments, the graft material 22 is positioned between both the posterior sheath 20 and rectus abdominus muscle 22 and the anterior sheath 21 and rectus abdominus muscle 22. In addition, the graft material 10 can be positioned and maintained in this location without the need for active fixation using sutures or other fixation systems.

Figure 6:
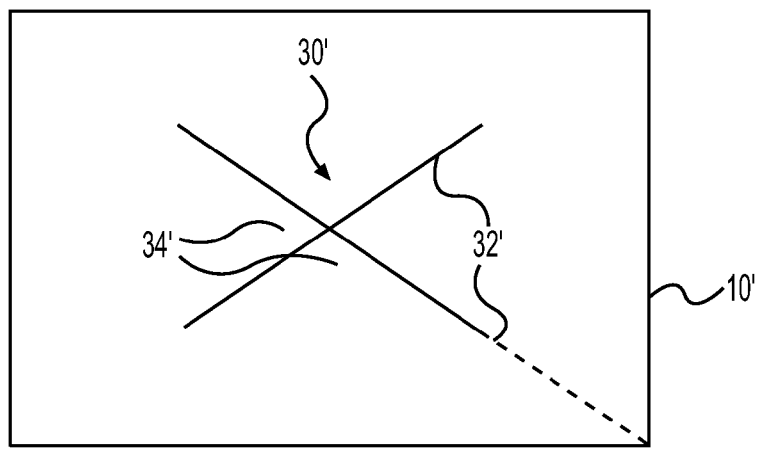
FIG. 6 is a top view of an exemplary embodiment of a graft material for repairing parastomal hernia, according to certain embodiments.

In some embodiments, repair of a parastomal hernia may be performed without removing the existing stoma. In such cases, the stoma site is first accessed using an open or laproscopic procedure, and the herniated abdominal content is removed from the opening in the abdominal wall. If necessary, diseased or injured tissue may be resected. Next, a space is created between a portion of the rectus sheath 20, 21 and rectus abdominus muscle 22. As above, this can be done using blunt dissection. After this space is created, graft material 10' is positioned in the space to reinforce the tissue around the stoma. As shown in FIG. 6, graft material 10' has an elongated slit 11 that extends from the central opening 30' to a periphery of the material, which allows the surgeon to positioned the graft around the hollow organ 8. In some embodiments, the graft material 10' further includes an "x"-shaped opening 30' forming tabs 34'. As described above, tabs 34' can be positioned along the sidewalls of the hollow organ forming the stoma, thereby providing support to the organ sidewalls. In some embodiments, the opening 30 is circular and a slit extends from the opening to a periphery of the material.

In some embodiments, a parastomal hernia can be repaired by repositioning or temporarily removing the stoma. For example, in some embodiments, the ostomy may be disengaged from surrounding tissue to allow placement of the graft material between the surrounding rectus sheath and muscular tissue. After the graft material is positioned, the ostomy may be reformed by passing the portion of the hollow organ through the graft material to traverse the abdominal wall and reform the stoma. In other embodiments, parastomal hernia is repaired by relocating the stoma to a different quadrant of the abdomen. In such a case, the original stoma site may be repaired by positioning a graft material 10 between the surrounding rectus sheath and muscle in order to prevent the risk of incisional hernia at the original stoma site, followed by closure of the primary stoma opening. Subsequently, graft material 10 is positioned in the new stoma site to lower the risk of hernia at the new site, using procedures described herein.

In some embodiments, the methods and devices of the present disclosure can be used to treat temporary ostomies. In other embodiments, the methods and devices can be used to treat ostomies that are intended to be long term or permanent.

It should be understood that the foregoing description is intended merely to be illustrative, and that any other equivalents, embodiments and modifications of the invention will be apparent to those skilled in the art from consideration of the specification and practice of the devices and methods disclosed herein.

What is claimed is:

1. A method of preventing parastomal hernia, comprising:
   selecting a graft material for reinforcement of a stoma site;
   forming an opening in an abdominal wall traversing the rectus abdominus;
   dissecting a space between the rectus abdominus muscle and a rectus sheath of the abdominal wall surrounding the opening;
   inserting the graft material into the space between the rectus abdominus muscle and the rectus sheath;
   passing a portion of a hollow organ through the graft material and the opening in the abdominal wall to form a stoma between the hollow organ and the abdominal wall with the graft material surrounding the hollow organ; and
   attaching a portion of the hollow organ to the abdominal wall to produce an ostomy, the graft material is not actively fixed to the rectus abdominus muscle or the rectus sheath.

2. The method of claim 1, wherein the space is formed between a posterior rectus sheath and the rectus abdominus muscle.

3. The method of claim 1, wherein the space is formed between an anterior rectus sheath and the rectus abdominus muscle.

4. The method of claim 1, wherein the space is formed between an anterior rectus sheath and the rectus abdominus muscle and a posterior rectus sheath and the rectus abdominus muscle, and wherein a first graft material is inserted into the space between the anterior rectus sheath and the rectus abdominus muscle and a second graft material is inserted into the space between the posterior rectus sheath and the rectus abdominus muscle.

5. The method of claim 1, wherein the graft material is non-synthetic.

6. The method of claim 1, wherein the graft material is an acellular tissue matrix.

7. The method of claim 6, wherein the graft material is a dermal matrix.

8. The method of claim 1, wherein the graft material is inserted into the space through the opening in the abdominal wall.

9. A method of repairing a parastomal hernia, comprising:
selecting a graft material for reinforcement of a stoma site;
dissecting a space between the rectus abdominus muscle and the rectus sheath of the abdominal wall surrounding a stoma site;
inserting the graft material into the space between the rectus abdominus muscle and the rectus sheath to surround the stoma site;
wherein the graft material is not actively fixed to the rectus abdominus muscle or the rectus sheath.

10. The method of claim 9, wherein the space is formed between a posterior rectus sheath and the rectus abdominus muscle.

11. The method of claim 9, wherein the space is formed between an anterior rectus sheath and the rectus abdominus muscle.

12. The method of claim 9, wherein the space is formed between an anterior rectus sheath and the rectus abdominus muscle and a posterior rectus sheath and the rectus abdominus muscle, and wherein a first graft material is inserted into the space between the anterior rectus sheath and the rectus abdominus muscle and a second graft material is inserted into the space between the posterior rectus sheath and the rectus abdominus muscle.

13. The method of claim 9, wherein the graft material is non-synthetic.

14. The method of claim 9, wherein the graft material is an acellular tissue matrix.

15. The method of claim 14, wherein the graft material is a dermal matrix.

16. The method of claim 9, further including detaching the stoma from the abdominal wall before inserting the graft material into the space between the rectus abdominus muscle and the rectus sheath to surround the stoma site;
passing a portion of a hollow organ forming the stoma through the graft material and an opening in the abdominal wall to reform a stoma between the hollow organ and the abdominal wall with the graft material surrounding the hollow organ; and
attaching a portion of the hollow organ to the abdominal wall to produce an ostomy.

* * * * *